(12) United States Patent
Martens et al.

(10) Patent No.: US 7,754,933 B2
(45) Date of Patent: Jul. 13, 2010

(54) REJUVENATING DEACTIVATED MOLECULAR SIEVE

(75) Inventors: Luc R. M. Martens, Meise (BE);
Marcel J. Janssen, Kessel-Lo (BE);
Nicolas Coute, Houston, TX (US);
James R. Lattner, La Porte, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 684 days.

(21) Appl. No.: 11/807,450

(22) Filed: May 29, 2007

(65) Prior Publication Data

US 2008/0015402 A1    Jan. 17, 2008

Related U.S. Application Data

(60) Provisional application No. 60/830,656, filed on Jul. 13, 2006.

(51) Int. Cl.
*C07C 1/00* (2006.01)
*B01J 21/20* (2006.01)
*B01J 38/02* (2006.01)

(52) U.S. Cl. .................. 585/640; 585/639; 502/20; 502/56

(58) Field of Classification Search .................. 585/639, 585/640; 502/20, 56
See application file for complete search history.

(56) References Cited

U.S. PATENT DOCUMENTS

| | | | |
|---|---|---|---|
| 6,316,683 B1 | 11/2001 | Janssen et al. | |
| 6,380,119 B1 * | 4/2002 | Grosch et al. | ............ 502/49 |
| 6,498,120 B1 | 12/2002 | Janssen et al. | |
| 6,537,941 B2 | 3/2003 | Janssen et al. | |
| 6,825,391 B2 | 11/2004 | Janssen et al. | |
| 2005/0038306 A1 | 2/2005 | Beech et al. | |

OTHER PUBLICATIONS

Paulitz et al., Microporous Materials, 2, 223-228 (1994).

* cited by examiner

*Primary Examiner*—In Suk Bullock

(57) ABSTRACT

This invention is directed to a method of rejuvenating a molecular sieve that has decreased catalytic activity as a result of contact with moisture, and a method of using the rejuvenated catalyst to make an olefin product from methanol feed. The molecular sieve can be rejuvenated by heating at a rate sufficient to increase the catalytic activity of the molecular sieve. The molecular sieve is considered to be rejuvenated when the molecular sieve has a CMCPS that is increased by at least 5% relative to that at a heat rate basis of 40° C./min over a temperature range of from 25° C. to 475° C.

45 Claims, No Drawings

REJUVENATING DEACTIVATED MOLECULAR SIEVE

CROSS-REFERENCE TO RELATED APPLICATIONS

This application claims the benefit of priority to U.S. Provisional Patent Application No. 60/830,656, filed Jul. 13, 2006, the disclosure of which is incorporated by reference.

FIELD OF THE INVENTION

This invention is directed to a method of rejuvenating molecular sieve that has decreased catalytic activity as a result of contact with moisture, and a method of using the rejuvenated catalyst to make an olefin product from methanol feed. In particular, the invention is directed to rejuvenating the molecular sieve by heating at a heat rate to increase its catalytic activity.

BACKGROUND OF THE INVENTION

Certain molecular sieve catalysts, such as silicoaluminophosphate (SAPO) molecular sieves molecular sieve catalysts, are particularly susceptible to structural changes as a result of continued exposure to even low levels of moisture. Although such authorities as Paulitz et al., *Microporous Materials*, 2, 223-228 (1994), have shown through X-ray diffraction (XRD), nuclear magnetic resonance (NMR), infrared (IR) and nitrogen ($N_2$) adsorption analyses that the structural change is largely reversible, such X-ray diffraction type studies have been found to be unreliable in determining loss of catalytic activity. For example, U.S. Pat. No. 6,316,683 (Janssen) indicates although such adsorption analyses show that structural change is largely reversible, that type of data cannot be relied upon as an indicator of loss of catalytic activity. According to Janssen, SAPO molecular sieve, as well as the SAPO molecular sieve blended with other catalyst material, can be protected from negative effects of moisture by properly shielding catalytic sites within the molecular sieve. Proper shielding can be accomplished in a variety of ways, including maintaining a template within the molecular sieve, covering the catalytic sites with a carbonaceous material or maintaining the sieve, even without a template, in an anhydrous environment.

U.S. Pat. Nos. 6,825,391 and 6,498,120 disclose another method of rejuvenating a SAPO molecular sieve. The method includes contacting a molecular sieve having a methanol uptake of less than 1, or a catalyst containing molecular sieve having a methanol up of less than 1, with anhydrous liquid or vapor until the methanol uptake ratio is increased by at least 10%. The rejuvenated molecular sieve or catalyst can be used to make an olefin product from an oxygenate-containing feedstock.

U.S. Pat. No. 6,537,941 also discloses a method of rejuvenating a SAPO molecular sieve. The method includes freeze drying a molecular sieve having a methanol conversion ratio of less than 1, or a catalyst containing molecular sieve and a binder having a methanol conversion ratio of less than 1. The rejuvenated molecular sieve or catalyst is used to make an olefin product from an oxygenate, and the olefin product can be separated into components that include ethylene and propylene, which can be used to make polyethylene and polypropylene, respectively.

U.S. Patent Publication No. 2005/0038306 details methods of starting up reaction systems that use metalloaluminophosphate molecular sieve catalysts that are susceptible to loss of catalytic activity due to contact with water molecules. The methods include loading activated catalyst into a reaction system and maintaining the catalyst at conditions so as to minimize or avoid loss of catalytic activity, until feed is fully introduced into the reaction system. In one embodiment, the reaction system is heated prior to introduction of the activated catalyst into the system. Alternatively, conditions of temperature of the catalyst, water partial pressure of the reaction system, and time of contact with water molecules are controlled so that loss of catalytic activity is not significant. These conditions are controlled so that the activated catalyst adsorbs little if any water. The greater the amount of water adsorbed, the greater the rate of deactivation of the catalyst.

The loss of molecular sieve catalytic activity as a result of contact with moisture presents a particular problem in the commercial production-to-use chain where storage and transport of molecular sieve and catalyst can take relatively long periods of time. For example, it is possible that molecular sieve or catalyst containing molecular sieve can be stored anywhere from 12 hours to many months, perhaps as long as one year before its use in a catalytic process. This stored sieve or catalyst is likely not to have a template within its internal pore structure as a result of having been removed by calcination prior to storage. Such a sieve or catalyst would be especially susceptible to damage by contact with moisture. Even partial loss of catalytic activity is of particular concern in large scale catalytic processes, which can include processes having a reactor loading in excess of 50 kg, particularly those in excess of 500 kg, and especially those in excess of 5000 kg. It would be particularly beneficial to find additional and more efficient ways in which to protect against loss of molecular sieve catalytic activity as a result of contact with moisture.

SUMMARY OF THE INVENTION

In order to overcome the various problems associated with decrease of activity of a molecular sieve due to contact by moisture, this invention provides a way to reverse such decrease, i.e., to rejuvenate the molecular sieve. In general, this invention provides a method of rejuvenating molecular sieve. The molecular sieve that is to be rejuvenated contains active catalytic sites and [$AlO_4$] and [$SiO_4$] tetrahedral units, and has decreased catalytic activity as a result of contact with moisture. The method includes providing the molecular sieve that is to be rejuvenated and heating the molecular sieve at a heat rate sufficient to rejuvenate the sieve. Preferably, the sieve is heated at a heat rate of greater than 40° C./min until the molecular sieve has a CMCPS that is increased by at least 5% relative to that at a heat rate basis of 40° C./min over a temperature range of from 25° C. to 475° C., thereby forming a rejuvenated molecular sieve.

In a preferred embodiment, the provided molecular sieve is heated at a heat rate of greater than 40° C./min until the molecular sieve has a CMCPS that is increased by at least 8% relative to that at a heat rate basis of 40° C./min over a temperature range of from 25° C. to 475° C. More preferably, the provided molecular sieve is heated at a heat rate of greater than 40° C./min until the molecular sieve has a CMCPS index that is increased by at least 10% relative to that at a heat rate basis of 40° C./min over a temperature range of from 25° C. to 475° C. Still more preferably, the provided molecular sieve is heated at a heat rate of at least 80° C./min until the molecular sieve has a CMCPS index that is increased by at least 5% relative to that at a heat rate basis of 40° C./min over a temperature range of from 25° C. to 475° C. Even more preferably, the provided molecular sieve is heated at a heat rate of at least 100° C./min until the molecular sieve has a CMCPS index that is increased by at least 5% relative to that at a heat rate basis of 40° C./min over a temperature range of from 25° C. to 475° C.

In one embodiment of the invention, the provided molecular sieve has a CMCPS index of less than 1. Preferably, the provided molecular sieve has a CMCPS index of less than 0.9. More preferably, the provided molecular sieve has a CMCPS index of less than 0.8.

In another embodiment, the provided molecular sieve is provided from a storage container and heated in a heating unit. Preferably, the heating unit is a calciner.

In another embodiment, the provided molecular sieve includes [$PO_4$] tetrahedral units. Preferably, the provided molecular sieve has a chabazite or AEI framework, or a mixture or intergrowth containing a chabazite and AEI framework.

In one embodiment of the invention, the provided molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferably, the provided molecular sieve is selected from the group consisting of SAPO-18, SAPO-34, SAPO-35, SAPO-44, SAPO-47, the metal containing forms thereof, and mixtures thereof. More preferably, the provided molecular sieve is selected from the group consisting of SAPO-18 and SAPO-34, the metal containing forms thereof, and mixtures thereof.

The rejuvenated molecular sieve can be used in any number of reaction processes. Preferably, the rejuvenated molecular sieve is contacted with oxygenate to form an olefin product.

DETAILED DESCRIPTION OF THE INVENTION

I. Rejuvenation of Molecular Sieve

This invention provides for the rejuvenation of molecular sieve which exhibits decreased catalytic activity as a result of contact with moisture. The molecular sieve can be rejuvenated by heating at a rate sufficient to increase the catalytic activity of the molecular sieve. According to this invention, a catalyst that exhibits decreased catalytic activity as a result of contact with moisture can be determined by measuring the cumulative grams of methanol converted per gram of sieve (CMCPS). A molecular sieve having a CMCPS index of less than 1 is considered to be decreased in catalytic activity as a result of contact with moisture, and such a molecular sieve is capable of being rejuvenated.

The CMCPS is considered to be the amount of methanol converted (grs) per gram of catalyst over the total time the catalyst is active for methanol conversion. A molecular sieve or catalyst containing a molecular sieve is considered fully deactivated for methanol conversion if the measured methanol conversion is less than 5 wt %. The CMCPS is therefore a measure of the useful catalyst life.

The CMCPS index is determined using the CMCPS of calcined molecular sieve stored at 200° C. for 22 hours and heated at a heat rate of 40° C./sec over a temperature range of from 25° C. to 475° C. as the base case CMCPS. The CMCPS index is then the CMCPS at any given heat up rate divided by the base case CMCPS.

In this invention, a molecular sieve is considered to be rejuvenated when the molecular sieve has a CMCPS that is increased by at least 5% relative to that at a heat rate basis of 40° C./min over a temperature range of from 25° C. to 475° C. Preferably, the rejuvenated molecular sieve has a CMCPS that is increased by at least 8%, more preferably one that has been increased by at least 10%.

The lower the CMCPS uptake index of a molecular sieve, the more suitable the molecular sieve for rejuvenation. From an efficiency standpoint, it is preferable to rejuvenate a molecular sieve which has a CMCPS index of less than 1, more preferably less than 0.9, and most preferably less than 0.8. Complete rejuvenation results in a CMCPS index of 1.

In general, the faster the heat up rate, the greater the increase in CMCPS. Preferably, the molecular sieve that exhibits decreased catalytic activity as a result of contact with moisture is rejuvenated by heating the sieve or catalyst at a heat rate of greater than 40° C./min. More preferably, the molecular sieve is heated at a heat rate of at least 80° C./min, and still more preferably at a heat rate of at least 500° C./min, still more preferably at a heat rate of at least 500° C./min, even more preferably at least 1000° C./min, and most preferably at least 2000° C./min.

Any type of suitable heating unit can be used to appropriate heat and rejuvenate the molecular sieve. Non-limiting examples of such heating units include calciners, electrical ovens, belt calciners, rotay calciners, kilns, microwave ovens or an appropriate vessel of a reaction system, e.g., a regeneration vessel.

In one embodiment of the invention, moisture deactivated molecular sieve that has been stored in a storage container is provided to a heating unit and heated in the unit at a rate effective to rejuvenate the molecular sieve. The rejuvenated molecular sieve can then be added to a reaction system. According to this invention, the reaction system includes all vessels appropriate to carry out the reaction process, including the reactor, regenerator, and other vessels.

II. Molecular Sieve

This invention incorporates the use of catalyst containing one more types of molecular sieve compositions, particularly those types of molecular sieves that contain active catalytic sites that are susceptible to deactivation due to contact with water molecules. In general, molecular sieves have various chemical, physical, and framework characteristics, and have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001).

Crystalline molecular sieve materials all have a 3-dimensional, four-connected framework structure of corner-sharing $TO_4$ tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B. V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of preferred molecular sieves, particularly for converting an oxygenate containing feedstock into olefin(s), include AEI, AFI BEA, CHA, EDI, FAU, FER, GIS, LTA, LTL, MER, MFI, MOR, MTT, MWW and TON. In one preferred embodiment, the molecular sieve of the invention has an AEI topology or a CHA topology, or a combination thereof, most preferably a CHA topology.

The small, medium and large pore molecular sieves have from a 4-ring to a 12-ring or greater framework-type. Typically, the molecular sieves employed herein have 8-, 10- or 12-ring structures and an average pore size in the range of from about 3 Å to 15 Å. More typically, the molecular sieves used in this invention have 8-rings and an average pore size less than about 5 Å, such as in the range of from 3 Å to about 5 Å, for example from 3 Å to about 4.5 Å, and particularly from 3.5 Å to about 4.2 Å.

In one embodiment, molecular sieve crystals that are incorporated into the catalyst have a chabazite or AEI framework, or a mixture or intergrowth containing a chabazite and AEI framework. Preferably, the crystalline material also has a molar relationship of:

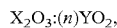
$$X_2O_3:(n)YO_2,$$

wherein X is a trivalent element, such as aluminum, boron, iron, indium, and/or gallium, preferably aluminum; Y is a tetravalent element, such as silicon, tin, titanium and/or germanium, preferably silicon; and n is greater than 10, preferably greater than 50, still more preferably greater than 100, preferably that ranges from about 10 to about 2000, more preferably from about 50 to about 600, most preferably from about 100 to about 300.

The molecular sieve that can be incorporated into the catalyst of this invention is prepared from a reaction mixture containing sources of water, an oxide of a trivalent element X, an oxide of a tetravalent element Y, and an organic templating agent or template. In general, templating agents or templates include compounds that contain elements of Group 15 of the Periodic Table of Elements, particularly nitrogen, phosphorus, arsenic and antimony. Typical templates also contain at least one alkyl or aryl group, such as an alkyl or aryl group having from 1 to 10 carbon atoms, for example from 1 to 8 carbon atoms. Preferred templates are nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templates include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2) octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone. Preferred templates are selected from the group consisting of tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine, heated degraded forms thereof, and combinations thereof. In one embodiment, the template is preferably selected from the group consisting of N-alkyl-3-quinuclidinol, N,N,N-trialkyl-1-adamantammonium cations, N,N,N-trialkyl-exoaminonorbornane and mixtures thereof, and is preferably a N,N,N-tri-methyl-1-adamantammonium cation.

In general, molecular sieve crystals that are incorporated into the catalyst have a molecular framework that includes [AlO$_4$] and [SiO$_4$] tetrahedral units. Such molecular sieves include aluminosilicates, as well as those molecular sieves that include other tetrahedral units such as [PO$_4$], such as silicoaluminophosphates. Preferably, the molecular sieves having framework that includes [AlO$_4$] and [SiO$_4$] tetrahedral units also have a chabazite or AEI framework, or a mixture or intergrowth containing a chabazite and AEI framework.

In another embodiment, molecular sieve crystals that are incorporated into the catalyst have a molecular framework that includes [AlO$_4$], [PO$_4$] and [SiO$_4$] tetrahedral units, such as silicoaluminophosphates (SAPO), and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the catalyst includes silicoaluminophosphate or metal-containing silicoaluminophosphate molecular sieve crystals. Preferably, the SAPO has a Si/Al ratio less than 0.65, such as less than 0.40, for example less than 0.32, and particularly less than 0.20. In one embodiment the molecular sieve has a Si/Al ratio in the range of from about 0.65 to about 0.10, such as from about 0.40 to about 0.10, for example from about 0.32 to about 0.10, and particularly from about 0.32 to about 0.15.

Non-limiting examples of SAPO molecular sieves useful herein include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56 and metal containing molecular sieves thereof. Of these, particularly useful molecular sieves are SAPO-18, SAPO-34, SAPO-35, SAPO-44, SAPO-56 and metal containing derivatives thereof. SAPO-34 is particularly preferred.

In another embodiment of the invention, the catalyst used in this invention incorporates aluminophosphate (AlPO) molecular sieves. These molecular sieves can be included as separate crystals or they can be intermixed with other crystalline structures such as by an intergrowth structure. Examples of aluminophosphates include AlPO-5, AlPO-11, AlPO-18, AlPO-31, AlPO-34, AlPO-36, AlPO-37 and AlPO-46.

In one embodiment, the catalyst includes a combination of at least one SAPO and at least one AlPO molecular sieve, wherein the SAPO is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47 and SAPO-56, and the AlPO is selected from the group consisting of AlPO-5, AlPO-11, AlPO-18, AlPO-31, AlPO-34, AlPO-36, AlPO-37 and AlPO-46. Preferably, the SAPO is SAPO-18 or SAPO-34, and preferably, the AlPO is AlPO-34 or AlPO-18.

The crystalline material or molecular sieve used in this invention can include at least in part a chabazite type framework and an AEI type framework or at least one intergrown phase of a CHA framework type and an AEI framework type. Intergrown molecular sieve phases are disordered planar intergrowths of molecular sieve frameworks. Reference is directed to the *Catalog of Disordered Zeolite Structures*, 2000 Edition, published by the Structure Commission of the International Zeolite Association and to the *Collection of Simulated XRD Powder Patterns for Zeolites*, M. M. J. Treacy and J. B. Higgins, 2001 Edition, published on behalf of the Structure Commission of the International Zeolite Association for a detailed explanation on intergrown molecular sieve phases.

Regular crystalline solids are built from structurally invariant building units, called Periodic Building Units, and are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

In the case of regular AEI and CHA framework type molecular sieves, the Periodic Building Unit is a double six ring layer. There are two types of layers "a" and "b," which are topologically identical except "b" is the mirror image of "a." When layers of the same type stack on top of one another, i.e. aaaaaaaa or bbbbbbbb, the framework type CHA is generated. When layers "a" and "b" alternate, ie, ababab, the framework type AEI is generated. Intergrown AEI/CHA molecular sieves comprise regions of CHA framework type sequences and regions of AEI framework type sequences. Each change from a CHA to an AEI framework type sequence results in a stacking fault. In addition, stacking faults can occur in a pure CHA phase material when a sequence of one mirror image layers intersects a sequence of the opposite mirror image layers, such as for example in aaaaaabbbbbbb.

Analysis of intergrown molecular sieves, such as AEI/CHA intergrowths, can be effected by X-ray diffraction and in particular by comparing the observed patterns with calculated patterns generated using algorithms to simulate the effects of stacking disorder. DIFFaX is a computer program based on a mathematical model for calculating intensities from crystals containing planar faults (see M. M. J. Tracey et al., *Proceedings of the Royal Chemical Society*, London, A [1991], Vol. 433, pp. 499-520). DIFFaX is the simulation program selected by and available from the International Zeolite Association to simulate the XRD powder patterns for randomly intergrown phases of zeolites (see *Collection of Simulated XRD Powder Patterns for Zeolites* by M. M. J. Treacy and J. B. Higgins, 2001, Fourth Edition, published on behalf of the Structure Commission of the International Zeolite Association). It has also been used to theoretically study intergrown phases of AEI, CHA and KFI, as reported by K. P. Lillerud et al. in *Studies in Surface Science and Catalysis*, 1994, Vol. 84, pp. 543-550.

Where the crystalline material of the invention comprises a mixture of CHA and AEI or an intergrowth of a CHA framework type molecular sieve and an AEI framework type molecular sieve, the material can possess a widely varying AEI/CHA ratio of from about 99:1 to about 1:99, such as from about 98:2 to about 2:98, for example from about 95:5 to 5:95. In one embodiment, where the material is to be used a catalyst in the conversion of oxygenates to olefins, the intergrowth is preferably CHA-rich and has AEI/CHA ratio ranging from about 5:95 to about 30:70. In addition, in some cases the intergrown material of the invention may comprise a plurality of intergrown phases each having a different AEI/CHA ratio. The relative amounts of AEI and CHA framework-type materials in the intergrowth of the invention can be determined by a variety of known techniques including transmission electron microscopy (TEM) and DIFFaX analysis, using the powder X-ray diffraction pattern of a calcined sample of the molecular sieve.

The molecular sieve can be incorporated or mixed with other additive materials. The combination of molecular sieve and other additive materials are generally referred to as formulated catalyst.

In one embodiment, another material resistant to the temperatures and other conditions employed in organic conversion processes is mixed with the molecular sieve. Such materials can include catalytically active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a catalytically active material tends to change the conversion and/or selectivity of the catalyst in the oxygenate conversion process. Inactive materials suitably serve as diluents to control the amount of conversion in the process so that products can be obtained in an economic and orderly manner without employing other means for controlling the rate of reaction. These materials can be incorporated into naturally occurring clays, e.g., bentonite and kaolin, to improve the crush strength of the catalyst under commercial operating conditions. The materials, i.e., clays, oxides, etc., function as binders for the catalyst. It is desirable to provide a catalyst having good crush strength because in commercial use it is desirable to prevent the catalyst from breaking down into powder-like materials.

Naturally occurring clays that can be employed include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Other useful binders include inorganic oxides, such as silica, zirconia, titania, magnesia, beryllia, alumina, and mixtures thereof.

In addition to the foregoing materials, the molecular sieve can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The relative proportions of molecular sieve and inorganic oxide matrix may vary widely, with the zeolite content ranging from about 1 to about 90 percent by weight and more usually, particularly when the composite is prepared in the form of beads, in the range of about 2 to about 80 weight percent of the composite.

III. Reaction Process Using Rejuvenated Molecular Sieve

The rejuvenated molecular sieve produced by this invention can be used in any of a variety of processes. In one embodiment, the rejuvenated molecular sieve is used in a the gas-to-olefins (GTO) process or, alternatively called, methanol-to-olefins (MTO) process. In such a process, the rejuvenated catalyst is contacted with oxygenate to form an olefin product. Preferably, an oxygenated feedstock is converted in the presence of a rejuvenated molecular sieve catalyst composition into one or more olefin(s). In particular, the feedstock contains one or more oxygenates, more specifically, one or more organic compound(s) containing at least one oxygen atom. Preferably, the oxygenate in the feedstock includes one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of specific types of oxygenates useful in the invention include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In a preferred embodiment, the feedstock contains at least one oxygenate selected from the group consisting of methanol, ethanol, dimethyl ether, and diethyl ether; more preferably the oxygenate feed contains methanol and/or dimethyl ether, and most preferably the oxygenate feed contains methanol.

The feedstock is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

According to the invention, the amount of olefin(s) produced, based on the total weight of hydrocarbon produced, is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The process can be conducted over a wide range of reactor temperatures. For example, average reactor temperatures are in the range of from about 200° C. to about 1000° C. Preferably, the average reactor temperatures are in the range of from about 250° C. to about 800° C.; more preferably from about 250° C. to about 750° C., or from about 300° C. to about 650° C., or from about 350° C. to about 600° C., and most preferably from about 350° C. to about 550° C.

Similarly, the process can be conducted over a wide range of pressures including autogenous pressure. Typically the partial pressure of the oxygenate exclusive of any diluent therein employed in the process is in the range of from about 0.1 kPaa to about 5 MPaa, such as from about 5 kPaa to about 1 MPaa, and preferably from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the total feedstock, including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec.

In one embodiment, the process is conducted as a fixed bed process. In a preferred embodiment, the process is carried out as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977.

Preferred reactor types are riser reactors generally described in *Riser Reactor, Fluidization and Fluid-Particle*

Systems, pages 48 to 59, F. A. Zenz and D. F. Othmo, Reinhold Publishing Corporation, New York, 1960, and U.S. Pat. No. 6,166,282 (fast-fluidized bed reactor.

In one embodiment, the process is conducted as a fluidized bed process or high velocity fluidized bed process utilizing a reactor system, a regeneration system and a recovery system. In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent (s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

Feedstock is fed to the reactor as a liquid or a vapor, or as a mixed vapor and liquid composition. In one embodiment, methanol is included in the feedstock, and the amount of methanol in the feed to the reactor is in the range of from 20 weight percent to about 98 weight percent, such as from about 40 weight percent to about 97 weight percent, or from about 50 weight percent to about 95 weight percent, based on the total weight of the feedstock including any diluent contained therein.

The feedstock entering the reactor system is preferably converted, partially or fully, in one or more reactors into a gaseous effluent that enters a disengaging vessel along with a coked catalyst composition. In one embodiment, cyclone(s) are provided within the disengaging vessel to separate the coked catalyst composition from the gaseous effluent containing olefin product. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

After separation of the gaseous effluent from the coked catalyst, the gaseous effluent is sent to a recovery section of the system where the olefins are separated into components parts. For example, ethylene and propylene, and well as any other olefin product, can be separated and recovered as separate products. The coked catalyst, which contains a carbonaceous layer that was formed during the conversion process, is recovered from the disengaging vessel and can be re-used as is or sent to a regenerator. In the regenerator, the coke or carbonaceous layer is removed by contacting the catalyst, which is still hot from the reaction process, with a regeneration gas to remove some or all of the coke deposit.

IV. Examples

A morpholine SAPO-34 (Si/Al$_2$=0.64) was calcined at 650° C. (5 hours in nitrogen; 3 hours in air) to remove the template. Part of the de-templated SAPO-34 was stored at 200° C. for 22 hours, while other parts were stored at room temperature (25° C.) at a relative humidity of 90% for (i) 22 hours and (ii) 9 days.

All samples were tested in a fixed bed reactor at 476° C., 25 WHSV and 25 psig methanol partial pressure for the conversion of methanol to olefins. Product analysis was performed with an online gas chromatograph (GC). The heat up rate to bring the reactor and catalyst from room temperature to 475° C. was varied between 40° C./sec to 40° C./min. The results are shown in the Table.

TABLE

| Stored | Heat-up rate | CMCPS | CMCPS Index | wt. ave. alkane | wt. ave. $C_2 + C_3$ product (%) |
|---|---|---|---|---|---|
| 200° C. | 40° C./sec | 8.1 ± 0.7 | 1 | 11.3 ± 0.4 | 64.5 ± 0.5 |
| 200° C. | 80° C./min | 6.2 | 0.8 | 13.3 | 62.5 |
| 200° C. | 40° C./min | 5.5 | 0.7 | 16.9 | 56.9 |
| 22 hr over water | 40° C./sec | 5.3 | 0.7 | 23.5 | 53.8 |
| 22 hr over water | 40° C./min | 3.2 | 0.4 | 24.9 | 52.3 |
| 9 days over water | 40° C./sec | 2.13 | 0.3 | 27.2 | 46.1 |
| 9 days over water | 40° C./min | 0.15 | 0.02 | 25 | 13.5 |

From the Table it is clear that a faster heat-up rate results in a higher CMCPS. Furthermore, a significant increase in the CMCPS index can be obtained using high heat-up rates for SAPO type catalysts which have been exposed to moisture.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention is further illustrated but not limited by the following embodiments.

This invention further relates to:

Embodiment 1

A method of rejuvenating molecular sieve that contains active catalytic sites and [AlO$_4$] and [SiO$_4$] tetrahedral units, and has decreased catalytic activity as a result of contact with moisture, comprising:

providing the molecular sieve that has decreased catalytic activity as a result of contact with moisture; and heating the molecular sieve at a heat rate of greater than 40° C./min until the molecular sieve has a CMCPS that is increased by at least 5% relative to that at a heat rate basis of 40° C./min over a temperature range of from 25° C. to 475° C., thereby forming a rejuvenated molecular sieve.

Embodiment 2

The method of embodiment 1, wherein the provided molecular sieve is heated at a heat rate of greater than 40° C./min until the molecular sieve has a CMCPS that is increased by at least 8% relative to that at a heat rate basis of 40° C./min over a temperature range of from 25° C. to 475° C.

Embodiment 3

The method of any of the preceding embodiments, wherein the provided molecular sieve is heated at a heat rate of greater than 40° C./min until the molecular sieve has a CMCPS index that is increased by at least 10% relative to that at a heat rate basis of 40° C./min over a temperature range of from 25° C. to 475° C.

Embodiment 4

The method of any of the preceding embodiments, wherein the provided molecular sieve is heated at a heat rate of at least 80° C./min until the molecular sieve has a CMCPS index that is increased by at least 5% relative to that at a heat rate basis of 40° C./min over a temperature range of from 25° C. to 475° C.

Embodiment 5

The method of any of the preceding embodiments, wherein the provided molecular sieve is heated at a heat rate of at least 100° C./min until the molecular sieve has a CMCPS index that is increased by at least 5% relative to that at a heat rate basis of 40° C./min over a temperature range of from 25° C. to 475° C.

Embodiment 6

The method of any of the preceding embodiments, wherein the provided molecular sieve has a CMCPS index of less than 1.

Embodiment 7

The method of embodiment 6, wherein the provided molecular sieve has a CMCPS index of less than 0.9.

Embodiment 8

The method of embodiment 7, wherein the provided molecular sieve has a CMCPS index of less than 0.8.

Embodiment 9

The method of any of the preceding embodiments, wherein the provided molecular sieve is provided from a storage container and heated in a heating unit.

Embodiment 10

The method of embodiment 9, wherein the heating unit is a calciner.

Embodiment 11

The method of any of the preceding embodiments, wherein the provided molecular sieve includes [$PO_4$] tetrahedral units.

Embodiment 12

The method of any of the preceding embodiments, wherein the provided molecular sieve has a chabazite or AEI framework, or a mixture or intergrowth containing a chabazite and AEI framework.

Embodiment 13

The method of any of the preceding embodiments, wherein the provided molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

Embodiment 14

The method of embodiment 13, wherein the provided molecular sieve is selected from the group consisting of SAPO-18, SAPO-34, SAPO-35, SAPO-44, SAPO-47, the metal containing forms thereof, and mixtures thereof.

Embodiment 15

The method of embodiment 14, wherein the provided molecular sieve is selected from the group consisting of SAPO-18 and SAPO-34, the metal containing forms thereof, and mixtures thereof.

Embodiment 16

The method of any of the preceding embodiments, wherein the rejuvenated molecular sieve is contacted with oxygenate to form an olefin product.

The invention claimed is:

1. A method of rejuvenating molecular sieve that contains active catalytic sites and [$AlO_4$] and [$SiO_4$] tetrahedral units, and has decreased catalytic activity as a result of contact with moisture, comprising:
   providing the molecular sieve that has decreased catalytic activity as a result of contact with moisture; and
   heating the molecular sieve at a heat rate of greater than 40° C./min until the molecular sieve has a CMCPS that is increased by at least 5% relative to that at a heat rate basis of 40° C./min over a temperature range of from 25° C. to 475° C., thereby forming a rejuvenated molecular sieve.

2. The method of claim 1, wherein the provided molecular sieve is heated at a heat rate of greater than 40° C./min until the molecular sieve has a CMCPS that is increased by at least 8% relative to that at a heat rate basis of 40° C./min over a temperature range of from 25° C. to 475° C.

3. The method of claim 1, wherein the provided molecular sieve is heated at a heat rate of greater than 40° C./min until the molecular sieve has a CMCPS index that is increased by at least 10% relative to that at a heat rate basis of 40° C./min over a temperature range of from 25° C. to 475° C.

4. The method of claim 1, wherein the provided molecular sieve is heated at a heat rate of at least 80° C./min until the molecular sieve has a CMCPS index that is increased by at least 5% relative to that at a heat rate basis of 40° C./min over a temperature range of from 25° C. to 475° C.

5. The method of claim 1, wherein the provided molecular sieve is heated at a heat rate of at least 100° C./min until the molecular sieve has a CMCPS index that is increased by at least 5% relative to that at a heat rate basis of 40° C./min over a temperature range of from 25° C. to 475° C.

6. The method of claim 1, wherein the provided molecular sieve has a CMCPS index of less than 1.

7. The method of claim 6, wherein the provided molecular sieve has a CMCPS index of less than 0.9.

8. The method of claim 7, wherein the provided molecular sieve has a CMCPS index of less than 0.8.

9. The method of claim 1, wherein the provided molecular sieve is provided from a storage container and heated in a heating unit.

10. The method of claim 9, wherein the heating unit is a calciner.

11. The method of claim 1, wherein the provided molecular sieve includes [PO$_4$] tetrahedral units.

12. The method of claim 1, wherein the provided molecular sieve has a chabazite or AEI framework, or a mixture or intergrowth containing a chabazite and AEI framework.

13. The method of claim 1, wherein the provided molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

14. The method of claim 13, wherein the provided molecular sieve is selected from the group consisting of SAPO-18, SAPO-34, SAPO-35, SAPO-44, SAPO-47, the metal containing forms thereof, and mixtures thereof.

15. The method of claim 14, wherein the provided molecular sieve is selected from the group consisting of SAPO-18 and SAPO-34, the metal containing forms thereof, and mixtures thereof.

16. The method of claim 1, wherein the rejuvenated molecular sieve is contacted with oxygenate to form an olefin product.

17. A method of rejuvenating molecular sieve that contains active catalytic sites and [AlO$_4$] and [SiO$_4$] tetrahedral units, and has decreased catalytic activity as a result of contact with moisture, comprising:
providing the molecular sieve that has decreased catalytic activity as a result of contact with moisture, wherein the molecular sieve is further characterized by having a CMCPS index of less than 1; and
heating the molecular sieve at a heat rate of greater than 40° C./min until the molecular sieve has a CMCPS that is increased by at least 5% relative to that at a heat rate basis of 40° C./min over a temperature range of from 25° C. to 475° C., thereby forming a rejuvenated molecular sieve.

18. The method of claim 17, wherein the provided molecular sieve has a CMCPS index of less than 0.9.

19. The method of claim 18, wherein the provided molecular sieve has a CMCPS index of less than 0.8.

20. The method of claim 17, wherein the provided molecular sieve is heated at a heat rate of greater than 40° C./min until the molecular sieve has a CMCPS that is increased by at least 8% relative to that at a heat rate basis of 40° C./min over a temperature range of from 25° C. to 475° C.

21. The method of claim 17, wherein the provided molecular sieve is heated at a heat rate of greater than 40° C./min until the molecular sieve has a CMCPS index that is increased by at least 10% relative to that at a heat rate basis of 40° C./min over a temperature range of from 25° C. to 475° C.

22. The method of claim 17, wherein the provided molecular sieve is heated at a heat rate of at least 80° C./min until the molecular sieve has a CMCPS index that is increased by at least 5% relative to that at a heat rate basis of 40° C./min over a temperature range of from 25° C. to 475° C.

23. The method of claim 17, wherein the provided molecular sieve is heated at a heat rate of at least 100° C./min until the molecular sieve has a CMCPS index that is increased by at least 5% relative to that at a heat rate basis of 40° C./min over a temperature range of from 25° C. to 475° C.

24. The method of claim 17, wherein the provided molecular sieve is provided from a storage container and heated in a heating unit.

25. The method of claim 24, wherein the heating unit is a calciner.

26. The method of claim 17, wherein the provided molecular sieve includes [PO$_4$] tetrahedral units.

27. The method of claim 17, wherein the provided molecular sieve has a chabazite or AEI framework, or a mixture or intergrowth containing a chabazite and AEI framework.

28. The method of claim 17, wherein the provided molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

29. The method of claim 28, wherein the provided molecular sieve is selected from the group consisting of SAPO-18, SAPO-34, SAPO-35, SAPO-44, SAPO-47, the metal containing forms thereof, and mixtures thereof.

30. The method of claim 29, wherein the provided molecular sieve is selected from the group consisting of SAPO-18 and SAPO-34, the metal containing forms thereof, and mixtures thereof.

31. The method of claim 17, wherein the rejuvenated molecular sieve is contacted with oxygenate to form an olefin product.

32. A method of making an olefin product from an oxygenate-containing feedstock, comprising:
providing a molecular sieve that contains active catalytic sites and [AlO$_4$] and [SiO$_4$] tetrahedral units and has decreased catalytic activity as a result of contact with moisture, and which has a CMCPS index of less than 1;
heating the molecular sieve at a heat rate of greater than 40° C./min until the molecular sieve has a CMCPS index that is increased by at least 5% relative to that at a heat rate basis of 40° C./min, thereby forming a rejuvenated molecular sieve; and
contacting the rejuvenated molecular sieve with an oxygenate-containing feedstock to produce an olefin product.

33. The method of claim 32, wherein the provided molecular sieve has a CMCPS index of less than 0.9.

34. The method of claim 33, wherein the provided molecular sieve has a CMCPS index of less than 0.8.

35. The method of claim 32, wherein the provided molecular sieve is heated at a heat rate of greater than 40° C./min until the molecular sieve has a CMCPS that is increased by at least 8% relative to that at a heat rate basis of 40° C./min over a temperature range of from 25° C. to 475° C.

36. The method of claim 32, wherein the provided molecular sieve is heated at a heat rate of greater than 40° C./min until the molecular sieve has a CMCPS index that is increased by at least 10% relative to that at a heat rate basis of 40° C./min over a temperature range of from 25° C. to 475° C.

37. The method of claim 32, wherein the provided molecular sieve is heated at a heat rate of at least 80° C./min until the molecular sieve has a CMCPS index that is increased by at least 5% relative to that at a heat rate basis of 40° C./min over a temperature range of from 25° C. to 475° C.

38. The method of claim 32, wherein the provided molecular sieve is heated at a heat rate of at least 100° C./min until the molecular sieve has a CMCPS index that is increased by at least 5% relative to that at a heat rate basis of 40° C./min over a temperature range of from 25° C. to 475° C.

39. The method of claim 32, wherein the provided molecular sieve is provided from a storage container and heated in a heating unit.

40. The method of claim 39, wherein the heating unit is a calciner.

41. The method of claim 32, wherein the provided molecular sieve includes [PO$_4$] tetrahedral units.

42. The method of claim 32, wherein the provided molecular sieve has a chabazite or AEI framework, or a mixture or intergrowth containing a chabazite and AEI framework.

43. The method of claim 32, wherein the provided molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof.

44. The method of claim 43, wherein the provided molecular sieve is selected from the group consisting of SAPO-18, SAPO-34, SAPO-35, SAPO-44, SAPO-47, the metal containing forms thereof, and mixtures thereof.

45. The method of claim 32, wherein the provided molecular sieve is selected from the group consisting of SAPO-18 and SAPO-34, the metal containing forms thereof, and mixtures thereof.

* * * * *